United States Patent [19]
Chauvette et al.

[11] 4,281,117
[45] Jul. 28, 1981

[54] PROCESS FOR 3-CHLORO CEPHALOSPORIN NUCLEUS

[75] Inventors: Pamela A. Chauvette; Robert R. Chauvette, both of Indianapolis, Ind.

[73] Assignee: Eli Lilly and Company, Indianapolis, Ind.

[21] Appl. No.: 183,918

[22] Filed: Sep. 4, 1980

[51] Int. Cl.$^3$ ............................................ C07D 501/04
[52] U.S. Cl. ..................................... 544/016; 424/246
[58] Field of Search .................. 544/16; 260/245.2 R; 424/246

[56] References Cited

U.S. PATENT DOCUMENTS

| | | | |
|---|---|---|---|
| 4,064,343 | 12/1977 | Chauvette | 544/16 |
| 4,115,643 | 9/1978 | Kukolja et al. | 544/16 |
| 4,223,133 | 9/1980 | Bunnell | 544/16 |
| 4,226,986 | 10/1980 | Matfield et al. | 544/16 |

OTHER PUBLICATIONS

J. Altman et al., "7-N-Amidinocephalosporins", J. Med. Chem., 1975, vol. 18, No. 6, pp. 627–630.
F. J. Lund, "6β-Amidinopenicillanic Acids–Synthesis and Antibacterial Properties", Recent Advances in the Chemistry of β-Lactam Antibiotics, Ed. J. Elks, Specialist Publication–Chemical Society, No. 28, 1977, pp. 25–45.
B. Baltzer et al., "Degradation of Mecillinam in Aqueous Solution", J. Pharm. Sci., 68, No. 10, Oct. 1979, pp. 1207–1215.

Primary Examiner—Nicholas S. Rizzo
Attorney, Agent, or Firm—William B. Scanlon; Arthur R. Whale

[57] ABSTRACT

7-Amino-3-hydroxy-3-cephem esters react with a chlorinating agent, e.g. phosgene, thionyl chloride and preferably PCl$_3$-DMF to provide 7β-[(dimethylaminomethylene)amino]-3-chloro-3-cephem esters which on reaction with a carboxylic acid, a percarboxylic acid, or a phenol, having a pH in water of about 2–5, afford 7β-formamido-3-chloro-3-cephem esters, and corresponding 2-cephem esters. Percarboxylic acids provide 7β-formamido-3-chloro-3-cephem ester 1-oxides. The 7-formamido derivatives provide the 7-amino-3-chloro-3-cephem ester on acid hydrolysis. The 7-amino-3-chloro esters are useful for preparing antibiotics.

12 Claims, No Drawings

PROCESS FOR 3-CHLORO CEPHALOSPORIN NUCLEUS

BACKGROUND OF THE INVENTION

Among the newer cephalosporin antibiotics introduced into clinical medicine is cefaclor. Cefaclor is a broad spectrum antibiotic which is administered orally and is highly effective in the treatment of human infections. Cefaclor, known chemically as 7-D-phenylglycylamido-3-chloro-3-cephem-4-carboxylic acid, is described and claimed in U.S. Pat. No. 3,925,372. Cefaclor can be prepared by the acylation of the "3-chloro nucleus", 7-amino-3-chloro-3-cephem-4-carboxylic acid or an ester thereof. The 3-chloro nucleus in the free amino acid form is represented by the following formula

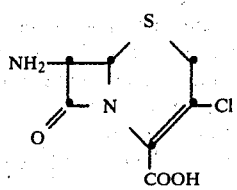

This nucleus, and the esters thereof, are valuable intermediates useful in the overall synthesis of cefaclor and in the preparation of other 3-halo substituted cephalosporins. The 3-chloro nucleus and other 3-halo nuclei are claimed and described in U.S. Pat. No. 4,064,343.

Prior to the present invention the 3-chloro nucleus was obtained by the N-deacylation of a 7-acylamino-3-chloro cephalosporin ester as described by U.S. Pat. No. 4,064,343. While 7-acylamino-3-chloro cephalosporins are prepared by chlorinating a 7-acylamino-3-hydroxy cephalosporin with phosphorus trichloride in DMF, the chlorination of a 7-amino-3-hydroxy cephalosporin ester with PCl$_3$/DMF results in the formation of a 7-[(dimethylaminomethylene)amino]3-chloro nucleus ester. The dimethylaminomethylene group, however, proved refractory to numerous cleavage attempts. Because of the importance of these cephalosporin nuclei, alternative routes to their preparation can be of significance in the commercial manufacture of the 3-halo substituted cephalosporin antibiotics.

The present invention provides an alternative process for the preparation of the 3-chloro nucleus. In particular, it provides a process for the direct conversion of a 7-amino-3-hydroxy-3-cephem-4-carboxylic acid ester, the "3-hydroxy nucleus" to the readily hydrolyzed N-formyl derivative of the 3-chloro nucleus.

SUMMARY OF THE INVENTION

This invention relates to a process for the preparation of 7-amino-3-chloro-3-cephem-4-carboxylic acid and esters thereof and to useful intermediates. In particular, it relates to a process for preparing the 3-chloro nucleus which comprises reacting a 7-amino-3-hydroxy-3-cephem ester with a chlorinating agent, for example phosphorus trichloride, in dimethylformamide to produce a 7β-[(dimethylaminomethylene)amino]-3-chloro-3-cephem ester which, on reaction with a carboxylic acid, a percarboxylic acid, or a phenol having a pH in water of between about 2.0 and about 5, forms the corresponding 7β-formamido-3-chloro ester. The product is obtained as an isomeric mixture of 7β-formamido-3-chloro-3-cephem and the corresponding 2-cephem when the 7-amidino-3-chloro intermediate is reacted with a weakly acidic carboxylic acid or with a phenol.

The isomeric mixture can be oxidized to the sulfoxide with a peracid to convert the 2-cephem present in the mixture to the 3-cephem sulfoxide. The 3-cephem sulfoxide ester is then reduced to provide the desired 7β-formamido-3-chloro-3-cephem-4-carboxylic acid ester.

When the 7-amidino-3-chloro intermediate is reacted with a weakly acidic percarboxylic acid a 7β-formamido-3-chloro-3-cephem-1-oxide is obtained and can be reduced to the desired 3-cephem in the sulfide form.

The 7β-formamido group can then be hydrolyzed with dilute acid to provide the desired 7-amino-3-chloro-3-cephem ester.

DETAILED DESCRIPTION

The process of this invention provides an overall method for converting a 3-hydroxy nucleus ester to a 3-chloro nucleus ester. The process of this invention comprises reacting in substantially dry dimethylformamide a 7-amino-3-hydroxy-3-cephem ester represented by the formula

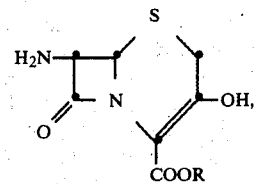

with between about 2 to about 6 moles of chlorinating agent per mole of the 7-amino-3-hydroxy cephem ester to provide the corresponding ester of a 7β-[(dimethylaminomethylene)amino]-3-chloro-3-cephem-4-carboxylic acid represented by the formula

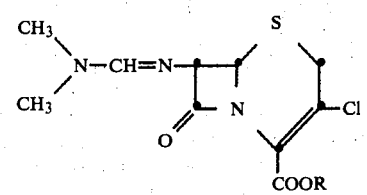

The 3-chloro ester is then reacted in an inert solvent with between about 1 mole and about 6 moles per mole of the 3-chloro ester of a carboxylic acid, a percarboxylic acid, or a phenol having a pH in water of about 2 to about 5 to form a mixture of a 7β-formamido-3-chloro-3-cephem ester and the corresponding 3-chloro-2-cephem ester or a 7β-formamido-3-chloro-3-cephem-1-oxide ester represented by the formula

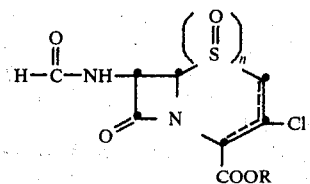

wherein n is 0 or 1, and when n is 0 the dotted bonding line indicates a mixture of the 3-cephem and 2-cephem isomers, and when n is 1 the dotted bonding indicates a 3-cephem.

The first step of the process is carried out at a temperature between about 15° C. and about 60° C. and preferably at about 20°–30° C.

Chlorinating agents which can be used in the process are selected from the group consisting of phosphorus trichloride, phosgene, oxalyl chloride, thionyl chloride, or a sulfonyl chloride represented by the formula $$R_2—SO_2—Cl$$

wherein $R_2$ is $C_1$–$C_4$ alkyl, phenyl, or phenyl substituted by halogen or methyl.

Examples of sulfonyl chlorides which can be used are the $C_1$–$C_4$ alkylsulfonyl chlorides such as methanesulfonyl chloride, ethanesulfonyl chloride, n-butanesulfonyl chloride, and like straight and branched chain sulfonyl chlorides; and the phenyl and substituted phenylsulfonyl chlorides such as benzenesulfonyl chloride, p-toluenesulfonyl chloride, p-chlorobenzenesulfonyl chloride, and the like.

The preferred chlorinating agent of this invention is phosphorus trichloride.

The process is carried out by adding the chlorinating agent to a solution of the 3-hydroxy nucleus ester in DMF. Alternatively the chlorinating agent can be added as a solution in DMF. The reaction can be carried out on the 3-hydroxy nucleus ester as the free amine or on a salt thereof such as the hydrochloride salt. A few drops of water can be used if necessary to achieve solubility of the salt form in DMF.

The first step of the process results in reaction at two sites of the 3-hydroxy nucleus ester. The 3-hydroxy group is replaced by chlorine and the 7-amino group is converted to an N,N-dimethylamidino group.

The second step of the process results in the degradation of the 7-amidino function to the hydrolyzable N-formyl group. The degradation is carried out with a mild acid. Carboxylic acids, percarboxylic acids or phenols each having a pH of between about 2 and about 5 as observed in water can be used. Examples of such acids are formic acid, acetic acid, propionic acid, benzoic acid, perbenzoic acid, m-chlorobenzoic acid, and m-chloroperbenzoic acid and like weak acids. Examples of such weakly acidic phenols include phenol, the cresols, m-chlorophenol, p-chlorophenol, o-chlorophenol, and like phenols which in water exhibit a pH of between about 2 and about 5.

Strong acids such as the mineral acids, for example, hydrochloric acid, and the stronger sulfonic acids for example benzenesulfonic acid, toluenesulfonic acid and p-chlorobenzenesulfonic acid form salts with the 7$\beta$-amidino function which fail to degrade to the 7$\beta$-formamido derivative in the process.

The mild acid degradation of the 7$\beta$-amidino substituted 3-chloro ester is carried out in an inert organic solvent at a temperature between about 20° C. and about 45° C. Solvents which can be used include for example ketones such as acetone, methylethyl ketone, and methylisobutyl ketone; esters such as methyl acetate, ethyl acetate, methyl propionate and n-butyl acetate; halogenated hydrocarbons such as methylene chloride, dichloroethane and trichloroethane; nitriles for example acetonitrile; and ethers such as tetrahydrofuran, tetrahydropyran, dioxane, and ethylene glycol dimethyl ether.

During the degradation with a carboxylic acid or a phenol, isomerization of the cephem bond from the 3,4-position to the 2,3-position occurs to a significant extent. The mixture of the isomeric 7$\beta$-formamido-3-chloro-3-cephem and 2-cephem esters is recovered from the reaction mixture as follows. The mixture is evaporated to dryness and the reaction product mixture is dissolved in a mixture of an organic solvent such as ethyl acetate and dilute aqueous acid. The dilute acid, extracts in the salt form, basic side products such as dimethylamine formed in the degradation. The solution of the product in the organic solvent is washed with water at an acid pH of 6 to 6.9, is dried and evaporated to provide the 7$\beta$-formamido-3-chloro-3-cephem ester and the corresponding 2-cephem ester as a mixture.

When the reaction product mixture is worked up at a basic pH, the 2-cephem ester isomer is obtained almost exclusively owing to further isomerization at the basic pH. For example, when the reaction mixture is evaporated to dryness and the crude reaction product mixture containing both 2-cephem and 3-cephem is dissolved in an organic solvent and is washed with a dilute aqueous base such as 5% sodium carbonate, only the 7$\beta$-formamido-3-chloro-2-cephem ester is obtained from the washed solution. In contrast an acid wash of the organic solution, as described above, yields a mixture of the isomers.

As mentioned above, when the mild acid degradation of the 7-amidino-3-chloro intermediate is carried out with a percarboxylic acid, the 7$\beta$-formamido-3-chloro-3-cephem ester 1-oxide is obtained without formation of the corresponding 2-cephem ester.

The two step process of this invention is illustrated by the following reaction scheme.

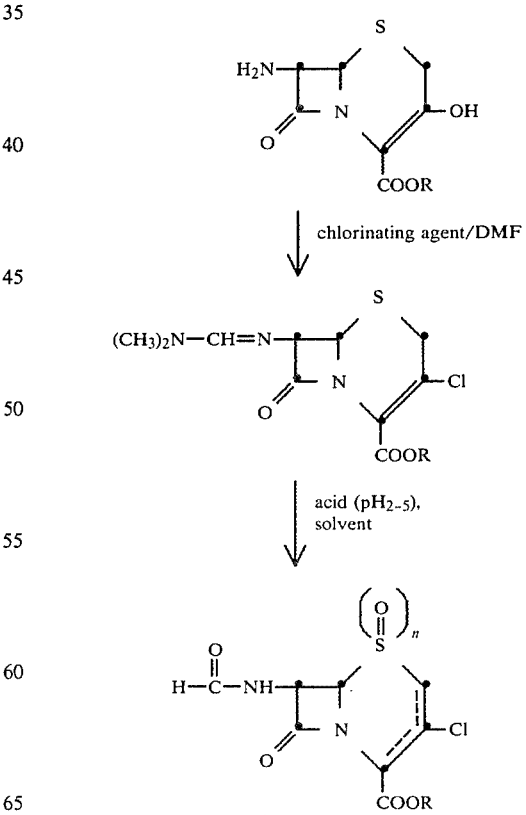

The term R in the above formulae represents a carboxy protecting ester group such as one of the ester forming groups commonly used to block or protect the C4 carboxylic acid group of the cephalosporins. Examples of such groups include benzyl and substituted benzyl such as p-methoxybenzyl, p-nitrobenzyl, and 2,4,6-trimethylbenzyl; diarylmethyl groups such as diphenylmethyl, 4-methoxydiphenylmethyl, and 4,4'-dimethoxydiphenylmethyl; and alkyl and substituted alkyl groups such as t-butyl, t-amyl, 2-iodoethyl, 2-bromoethyl, and 2,2,2-trichloroethyl. Such ester forming groups are functional groups in that they serve for the temporary protection of the carboxy group. After such use they are removed by known hydrolytic or reduction methods to provide the free carboxylic acid.

The 3-hydroxy-3-cephem ester employed as the starting material in the process is prepared as described in U.S. Pat. No. 3,917,587, issued Nov. 4, 1975.

As mentioned above, when a carboxylic acid or a phenol is used in the process the N-formyl 3-chloro product of the process is obtained as a mixture of the isomeric 2-cephem and 3-cephem and, under basic recovery conditions, as the 2-cephem isomer. The mixture of isomers or the 2-cephem isomer can be converted to the desired N-formyl 3-chloro-3-cephem ester by the known isomerization method which involves forming the sulfoxide of the 3-chloro ester followed by reduction back to the sulfide form. The formation of the sulfoxide causes the 2,3-double bond to isomerize to the 3,4-position (3-cephem). The isomerization is illustrated by the following reaction scheme.

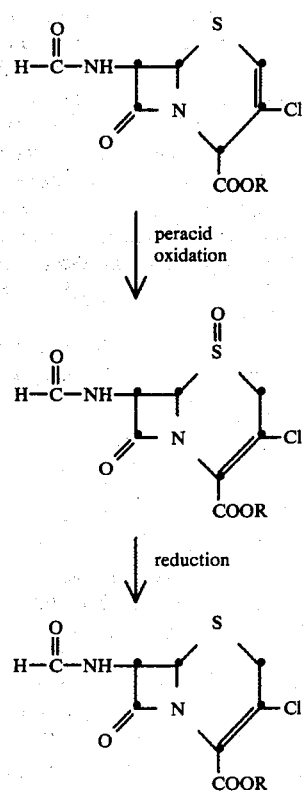

The formation of the sulfoxide can be carried out with a peracid such as peracetic, perbenzoic or preferably m-chloroperbenzoic acid in a suitable solvent such as acetone or methylene chloride. The 3-chloro-3-cephem ester sulfoxide is readily isolated by evaporation of the reaction mixture and dissolution of the reaction product mixture in an organic solvent such as ethyl acetate. The m-chlorobenzoic acid side product is washed from the solution with base and, after the solution of the product is dried and evaporated, the product can be further purified if desired by chromatography.

The reduction of the N-formyl 3-chloro-3-cephem ester can be carried out by known sulfoxide reduction methods. For example, the reduction methods described by Murphy et al., U.S. Pat. No. 3,641,014, and by Hatfield, U.S. Pat. No. 4,044,002. The latter method is an especially useful reduction method in that the recovery of the desired product is readily achieved.

The 7β-formamido-3-chloro-3-cephem-4-carboxylic acid ester is converted to the desired 7-amino-3-chloro-3-cephem ester by acid hydrolysis of the N-formyl group. The hydrolysis is carried out in a solvent such as methyl alcohol, tetrahydrofuran, or mixtures thereof with hydrochloric acid. For example, the N-formyl-3-chloro ester is dissolved in a mixture of methyl alcohol and tetrahydrofuran and the solution is treated at room temperature with a small amount of concentrated hydrochloric acid. The 7-amino-3-chloro nucleus ester is obtained as the hydrochloride salt.

In a further aspect of the invention there are provided the intermediates useful in the above process and represented by the following formula

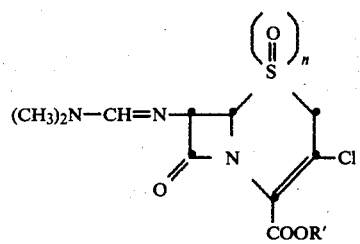

wherein R' is hydrogen or a carboxy-protecting group; n is 0 or 1, and salts thereof formed with a strong acid selected from the group consisting of hydrochloric acid, hydrobromic acid, sulfuric acid, phosphoric acid, or a sulfonic acid represented by the formula

A—SO$_2$OH wherein A is phenyl, tolyl, chlorophenyl, or naphthyl.

The compound of the above formula wherein R' is hydrogen is obtained by the de-esterification of a carboxy-protected ester derivative to either the salt form or free base form of the compound. The free acid compound can be used as the intermediate in the process which is preferably re-esterified with another ester moiety for conversion to the N-formyl product.

The carboxy-protecting ester groups, R', are the same carboxy-protecting groups defined for R above and include preferably p-nitrobenzyl, p-methoxybenzyl or diphenylmethyl.

The salts of the above formula formed with strong acids are stable salts useful for storage of quantities of the compound for subsequent use in the preparation of the 3-chloro nucleus by the process of this invention. As noted above the salts formed with strong acids are stable to chemical degradation of the 7-amidino side chain. Accordingly, these salts are converted to the free base form prior to use in the second step of the process.

The strong acid salts are prepared by treating a solution of the free base form of the compound of the above formula in an organic solvent with the strong acid or a solution of the acid in water or, an organic solvent in the case of the sulfonic acids. For example, the mineral acid salts such as the hydrochloride salt are prepared by adding the acid to a solution of the free base in a solvent such as acetone or ethyl acetate. the sulfonic acid salts are prepared by adding a solution of the sulfonic acid in a suitable solvent to a solution of the free base in a like solvent such as acetone or ethyl acetate.

Examples of the sulfonic acid strong acids used to prepare the above salts are benzenesulfonic acid, toluenesulfonic acid, α-naphthalenesulfonic acid, β-naphthalenesulfonic acid, p-chlorobenzenesulfonic acid and the like.

The following Examples further illustrate the present invention. In the Examples the following abbreviations are used. DMF is dimethylformamide, THF is tetrahydrofuran, and in the recitation of the nmr signals, s is singlet, m is multiplet, q is quartet, and d is doublet.

Melting points are uncorrected.

EXAMPLE 1 p-Nitrobenzyl 7β-[(dimethylaminomethylene)amino]-3-chloro-3-cephem-4-carboxylate p-Nitrobenzyl 7-amino-3-hydroxy-3-cephem-4-carboxylate hydrochloride salt (1.34 g. 3 mmole), was suspended in 85 ml of DMF and solubilized by adding 0.25 ml. of water to the suspension. To the solution were added 2.7 g. (1.7 ml., 20 mmole) of phosphorus trichloride and the mixture was stirred at room temperature for 3 hours. After the reaction was completed the the reaction mixture was dispersed into a mixture of ethyl acetate and water and the pH adjusted to 6.7 with 1 N sodium hydroxide. The ethyl acetate phase was separated, washed several times with water, dried over magnesium sulfate, and concentrated to a small volume in vacuo. When diethyl ether was added to the concentrate the product precipitated as a crystalline solid. The product was filtered and dried. There were obtained 725 mg. (57% yield) of the product melting at about 124° C. to about 128° C. with decomposition.

The following data were obtained with the product.

UV (acetonitrile): λ max 260 mμ ($\epsilon = 18,300$).

NMR (CDCl$_3$): signals (tau) at 7.08 (s, 6H, N(CH$_3$)$_2$), 6.34 (ABq, 2H, C$_2$—H$_2$), 5.0–4.5 (m, 4H, C$_6$—H, C$_7$—H, and ester methylene), 2.4–1.8 (s and q, N—CH=N and aromatic H).

Elemental analysis: calculated for C$_{17}$H$_{17}$N$_4$O$_5$SCl: Theory: C, 48.06; H, 4.03; N, 13.19; Cl, 8.34. Found: C, 48.32; H, 3.91; N, 12.96; Cl, 8.53.

EXAMPLE 2 p-Nitrobenzyl 7β-formamido-3-chloro-3- and 2-cephem-4-carboxylate

To a solution of 212 mg. (0.5 mmole) of p-nitrobenzyl 7β[(dimethylaminomethylene)amino]-3-chloro-3-cephem-4-carboxylate in 15 ml. of acetone were added 236 mg. (1.5 mmole) of m-chlorobenzoic acid and the mixture was stirred at room temperature for 16 hours. The reaction mixture was evaporated to dryness in vacuo and the residue containing the product was dissolved in a mixture of 5% hydrochloric acid and ethyl acetate. The organic layer was separated and slurried over water while the pH was adjusted to 6.8. The organic layer was separated, dried over magnesium sulfate, and evaporated to dryness in vacuo. Upon trituration of the residue with diethyl ether the product crystallized. The NMR spectra of the crystalline product run in DMSOd$_6$ and DMSOd$_6$-D$_2$O showed the product to be a mixture containing about 30% of p-nitrobenzyl 7β-formamido-3-chloro-3-cephem-4-carboxylate and about 70% of p-nitrobenzyl 7β-formamido-3-chloro-2-cephem-4-carboxylate.

EXAMPLE 3 p-Nitrobenzyl 7β-formamido-3-chloro-2-cephem-4-carboxylate p-Nitrobenzyl 7β-[(dimethylaminoethylene)-amino]-3-chloro-3-cephem-4-carboxylate was reacted with m-chlorobenzoic acid in acetone as described in Example 2 and the reaction mixture was evaporated to dryness. The residue obtained was dissolved in a mixture of ethyl acetate and 5% sodium carbonate. The organic layer was separated, dried over magnesium sulfate and evaporated in dryness in vacuo. Upon trituration of the residue with diethyl ether the product crystallized and was filtered. The NMR spectra of the product showed that it was the pure 2-cephem isomer.

Elemental analysis: calculated for C$_{15}$H$_{12}$N$_3$O$_6$SCl: Theory: C, 45.29; H, 3.04; N, 10.56. Found: C, 45.26; H, 3.15; N, 10.68.

EXAMPLE 4 p-Nitrobenzyl 7-amino-3-chloro-3-cephem-4-carboxylate hydrochloride salt

A solution of 500 mg. (1.13 mmole) of p-nitrobenzyl 7β-formyl-3-chloro-3-cephem-4-carboxylate in a solvent mixture of 7 ml. of dry THF and 9.6 ml. of methyl alcohol containing 1 ml. of concentrated hydrochloric acid was stirred at room temperature for 2.5 hours. During the reaction time the product precipitated as a crystalline solid. The product was filtered and dried. There were obtained 350 mg. (68% yield) of product. The following data were obtained for the product.

NMR (DMSOd$_6$): signal (tau) at 5.95 (s, 2H, C$_2$—H$_2$), 4.85–4.50 (m, 4H, C$_6$—H, ester CH$_2$, and C$_7$—H), 2.4–1.7 (q, 4H, aromatic H).

Elemental analysis: calculated for C$_{14}$H$_{13}$N$_3$O$_5$SCl$_2$: Theory: C, 41.39; H, 3.23; N, 10.34; Cl, 17.45. Found: C, 41.14; H, 3.13; N, 10.07; Cl, 17.46.

EXAMPLE 5 p-Nitrobenzyl 7β-[(dimethylaminomethylene)amino]-3-chloro-3-cephem-4-carboxylate hydrochloride To a solution of 12.8 g. (31.5 mmole) of p-nitrobenzyl 7-amino-3-chloro-3-cephem-4-carboxylate hydrochloride in 115 ml. of dry DMF were added with stirring 10.4 g (6.5 ml., 72 mmole) of phosphorus trichloride. The reaction mixture was stirred at room temperature for about 2 days and was then dispersed in a mixture of 5% aqueous sodium bicarbonate and ethyl acetate. The organic layer was separated and treated with 1 N hydrochloric acid. The title compound precipitated from solution and was filtered and dried under vacuum. There were obtained 11.3 g. (67% yield) of the salt.

EXAMPLE 6

The hydrochloride salt of p-nitrobenzyl 7-[(dimethylaminomethylene)amino]-3-chloro-3-cephem-4-carboxylate obtained as described in Example 5 was converted to the free base as follows.

A 6.3 g. sample of the hydrochloride salt was dissolved and stirred in a mixture of pH7 buffer and ethyl acetate. The organic layer was separated, washed with water, dried over magnesium sulfate and concentrated in vacuo to a small volume. The free base form crystallized from the concentrate and was filtered. There were obtained 3.2 g. of the free base. The mother liquor was further concentrated to yield a second crop of 1.7 g. of the free base.

The elemental analysis of the free base gave the following percent composition; calculated for $C_{17}H_{17}N_4O_5SCl$: Theory: C, 48.06; H, 4.03; N, 13.19. Found: C, 48.36; H, 4.26; N, 12.99.

EXAMPLE 7

7β-[(Dimethylaminomethylene)amino]-3-chloro-3-cephem-4-carboxylic acid

The title compound was obtained by the deesterification of the corresponding p-nitrobenzyl ester as follows.

p-Nitrobenzyl 7β-[(dimethylaminomethylene)-amino]-3-chloro-3-cephem-4-carboxylate (1.7 g., 14 mmole) was hydrogenated for one hour in methyl alcohol at room temperature under about 60 psi of hydrogen pressure in the presence of an equal weight (1.7 g.) of pre-reduced 5% palladium on carbon catalyst. After reduction was complete the catalyst was filtered and the filtrate was evaporated to dryness in vacuo. The residue was dissolved in a mixture of water and ethyl acetate and the pH of the mixture was adjusted to pH 7. The aqueous layer was separated, reslurried with ethyl acetate and the pH of the slurry adjusted to 2.5. The organic layer containing the product acid was separated, washed with water, dried over magnesium sulfate and evaporated to dryness in vacuo. The residue crystallized upon trituration with isopropyl alcohol. There were obtained 815 mg. (71% yield) of the crystalline free acid.

The following physical data were obtained for the free acid.

NMR (DMSOd$_6$) signals at (tau) 6.90 (d, 6H, N(CH$_3$)$_2$), 6.06 (ABq, 2H, C$_2$—H$_2$), 4.70 (d, 1H, C$_6$—H), 4.28 (d, 1H, C$_7$—H), 2.1 (broad s, COOH) and 1.70 (s, 1H, methine-H).

The spectrum also showed the presence of a trace of isopropanol.

Electrometric Titration (66 percent aqueous DMF) showed two pKa values of 4.2 and 7.7. The apparent molecular weight calculated from the titration data was 328.

I claim:

1. A process for preparing a compound of the formula

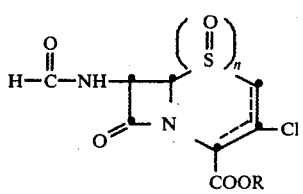

which comprises the steps a. reacting a 7-amino-3-hydroxy-3-cephem ester of the formula

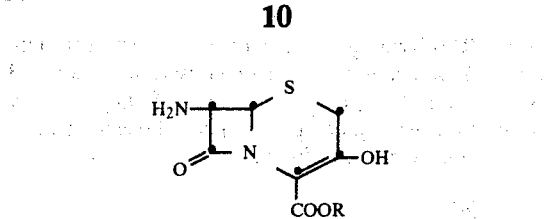

in substantially dry dimethylformamide at a temperature between about 15° C. and about 60° C. with between about 2 moles and about 6 moles of a chlorinating agent selected from the group consisting of phosphorus trichloride, phosgene, oxalyl chloride, thionyl chloride, or a sulfonyl chloride of the formula $R_2$—$SO_2$—Cl, b. recovering from said reaction a 7β-dimethylamidino-3-chloro-3-cephem ester of the formula

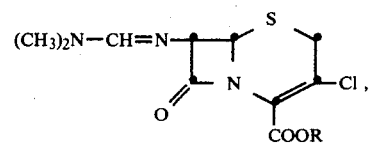

and c. adding to a solution of said 7β-amidino-3-chloro ester in an inert organic solvent at a temperature between about 20° C. and about 45° C. a carboxylic acid, percarboxylic acid, or a phenol each having a pH in water of between about 2 and about 5, wherein R in the above formulae is a carboxy-protecting group, n is 0 or 1, and when n is 0 the dotted bond indicates a double bond in the 2,3- and 3,4-positions, and when n is 1 the double bond is in the 3,4-position; and R$_2$ is C$_1$–C$_4$ alkyl, phenyl, or phenyl substituted by halogen or methyl, provided that, when n is 1, said percarboxylic acid is added in step c, and when n is 0, said carboxylic acid or said phenol is added in step c.

2. The process of claim 1 wherein phosphorus trichloride is the chlorinating agent.

3. The process of claim 1 wherein the 7β-amidino-3-chloro ester is treated with an acid selected from the group consisting of m-chloroperbenzoic acid, m-chlorobenzoic acid, formic acid and acetic acid.

4. The process of claim 3 wherein the acid is m-chlorobenzoic acid.

5. The process of claim 1 wherein R is p-nitrobenzyl, p-methoxybenzyl or diphenylmethyl.

6. The process of claim 5 wherein R is p-nitrobenzyl.

7. A compound of the formula

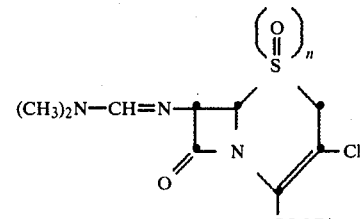

wherein R' is hydrogen or a carboxy-protecting group; n is 0 or 1; and salts thereof formed with a strong acid selected from the group consisting of hydrochloric acid, hydrobromic acid, sulfuric acid, phosphoric acid, or a sulfonic acid of the formula

A—SO₂OH wherein A is phenyl, chlorophenyl, tolyl, or naphthyl.

8. The compound of claim 7 in the free base form.
9. The compound of claim 7 wherein n is 1.
10. The compound of claim 7 wherein n is 0 and R' is hydrogen.
11. A strong acid salt of claim 7.
12. The salt of claim 11 said salt being p-nitrobenzyl 7β-[(dimethylaminomethylene)amino]-3-chloro-3-cephem-4-carboxylate hydrochloride.

* * * * *